(12) United States Patent
Andersson et al.

(10) Patent No.: US 7,002,037 B2
(45) Date of Patent: Feb. 21, 2006

(54) PROCESS FOR THE PREPARATION ON ENANTIOMERICALLY ENRICHED COMPOUNDS

(75) Inventors: Kjell Andersson, Mölndal (SE); Alan Eric Fischer, Biberstein (CH); Panagiotis Ioannidis, Södertälje (SE); Magnus Larsson, Södertälje (SE); Maria Larsson, Södertälje (SE); Sivaprasad Sivadasan, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 183 days.

(21) Appl. No.: 10/148,818

(22) PCT Filed: Nov. 29, 2000

(86) PCT No.: PCT/SE00/02382

§ 371 (c)(1),
(2), (4) Date: Nov. 13, 2002

(87) PCT Pub. No.: WO01/40159

PCT Pub. Date: Jun. 7, 2001

(65) Prior Publication Data

US 2003/0139474 A1 Jul. 24, 2003

(30) Foreign Application Priority Data

Dec. 3, 1999 (SE) ............................................. 9904415

(51) Int. Cl.
*C07C 261/00* (2006.01)
*C07C 59/48* (2006.01)

(52) U.S. Cl. ........................... 560/27; 560/60; 562/470
(58) Field of Classification Search .................... 560/27, 560/60; 562/470
See application file for complete search history.

(56) References Cited

U.S. PATENT DOCUMENTS

| 5,232,945 | A | | 8/1993 | Hulin |
| 5,306,725 | A | | 4/1994 | Sano et al. |
| 6,048,883 | A | | 4/2000 | Haigh et al. |
| 6,054,453 | A | | 4/2000 | Lohray et al. |
| 6,258,850 | B1 | | 7/2001 | Andersson |
| 6,362,360 | B1 | * | 3/2002 | Andersson et al. ........... 560/27 |
| 6,630,600 | B1 | | 10/2003 | Andersson et al. |
| 6,660,879 | B1 | | 12/2003 | Andersson |

FOREIGN PATENT DOCUMENTS

| WO | WO 9731907 | * | 9/1997 |
| WO | 9962870 | | 12/1999 |

OTHER PUBLICATIONS

Aitken et al., Synthesis, vol. 12, pp. 958–959 (1989).
Gramlich et al., Chem. Ber., vol. 112, pp. 1571–1584 (1979).
Sakamoto et al., Heterocycles, vol. 27, pp. 257–260 (1988).

* cited by examiner

*Primary Examiner*—Cecilia J. Tsang
*Assistant Examiner*—Taylor Victor Oh
(74) *Attorney, Agent, or Firm*—White & Case LLP

(57) ABSTRACT

The present invention relates to novel resolution methods, which are useful in the preparation of enantiomerically enriched intermediates which in their turn are useful in the prepartion of compounds with a pharmacological effect on the insulin resistance syndrome (IRS). It is such a process that the present inventions sets out to define, and more particularly for the preparation of the (S)-enantioner of certain 2-ethoxy-3-(4-hydroxyphenyl)propanoic acids and derivatives thereof.

39 Claims, No Drawings

PROCESS FOR THE PREPARATION ON ENANTIOMERICALLY ENRICHED COMPOUNDS

FIELD OF INVENTION

The present invention relates to novel resolution methods, which are useful in the preparation of enantiomerically enriched intermediates which in their turn are useful in the preparation of compounds with a pharmacological effect on the insulin resistance syndrome (IRS).

BACKGROUND OF INVENTION

Enantiomers can be produced using various techniques e.g. classical resolution by crystallisation of diastereomeric salts of the racemate, enzymatic resolution, chromatographic separation of the enantiomers, separation of the racemate by chiral chromatography as well as by different enantioselective synthetic techniques.

There is, however, a need to select a suitable combination of process steps as well as suitable conditions of each individual step in order to achieve an enantiomeric purity, which is sufficient to provide a pharmaceutically and economically feasible process.

It is such a process that the present invention sets out to define, and more particularly for the preparation of the (S)-enantiomer of certain 2-ethoxy-3-(4-hydroxyphenyl) propanoic acids and derivatives thereof.

SUMMARY OF INVENTION

The present invention relates to a process for the preparation of the (S)-enantiomer of a compound of the general formula I, comprising reacting a racemic compound according to the general formula II with a chiral amine, thereby forming a diastereomeric salt according to the general formula III, subsequently separating the diastereomers by crystallisation followed by removal of the amine and thereafter, if suitable or necessary, deprotecting the compound so obtained with a deprotecting agent. Optionally a free carboxylic acid function may in the end be protected with the group $R^P$.

The present invention further relates to a process for the preparation of the (S)-enantiomer of a compound of the general formula V, comprising reacting a racemic compound according to the general formula II with a chiral compound, thereby forming a diastereomeric mixture according to general formula IV, subsequently separating the diastereomers by chromatography and/or crystallisation, thereafter treating the resulting (S)-enantiomer of compound IV with a suitable reagent, e.g. an acid or base for removing the chiral auxiliary group, and thereafter, if desirable or necessary, deprotecting the resulting compound so obtained with a deprotecting agent. Optionally a free carboxylic acid function may in the end be protected with the group $R^P$.

The present invention further relates to a process for the preparation of the (S)-enantiomer of a compound of the general formula VII, comprising separating the enantiomers of a compound of the general formula VII by chiral chromatography and thereafter, if necessary, deprotecting the compound so obtained with a deprotecting agent.

The present invention further relates to a process for the preparation of a compound of the general formula VIII, comprising reducing a compound according to the general formula VI by for example hydrogenation in the presence of a suitable catalyst. Compound VIII can then be further processed as described above for compounds according to general formula I or V.

Another aspect of the invention is a compound of the general formula VI

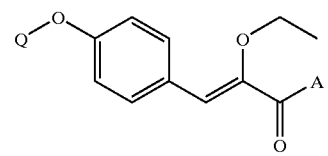

VI wherein Q is a protecting group or H, and A is OH, a chiral auxiliary group or the group $OR^P$, wherein $R^P$ is a protecting group and one or more of the hydrogen atoms of the phenyl group may be substituted by the equivalent number of halogen atoms.

DETAILED DESCRIPTION OF INVENTION

More specifically, the present invention relates to a process for the preparation of the (S)-enantiomer of a compound of the general formula I,

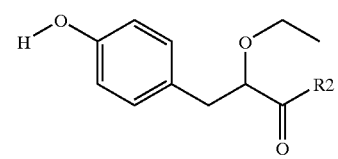

I wherein R2 is OH or the group $OR^P$, wherein $R^P$ is a protecting group, and one or more of the hydrogen atoms of the phenyl group are optionally substituted by the equivalent number of halogen atoms, comprising reacting a racemic compound according to the general formula II

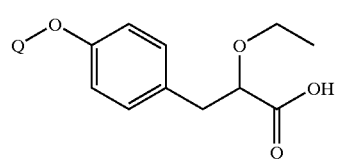

II wherein Q is a protecting group or H, and one or more of the hydrogen atoms of the phenyl group are optionally substituted by the equivalent number of halogen atoms, with a chiral amine, thereby forming a salt according to the general formula III

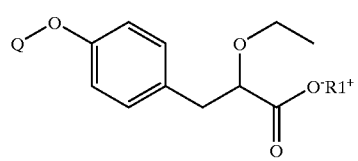

III wherein Q is a protecting group or H, and R1 is a chiral amine, and one or more of the hydrogen atoms of the phenyl group are optionally substituted by the equivalent number of halogen atoms, subsequently separating the diastereomers by crystallisation followed by removal of the amine, and thereafter, if desirable, deprotecting the Q group of the resulting compound with a deprotecting agent. Optionally a free carboxylic acid function may in the end be protected with the group $R^P$.

The present invention further relates to a process for the preparation of the S-enantiomer of a compound of the general formula V,

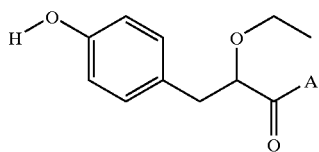

wherein A is OH, a chiral auxiliary group or the group $OR^P$, wherein $R^P$ is a protecting group, and one or more of the hydrogen atoms of the phenyl group are optionally substituted by the equivalent number of halogen atoms, comprising reacting a racemic compound according to the general formula II

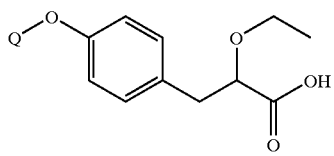

wherein Q is a protecting group or H, and one or more of the hydrogen atoms of the phenyl group are optionally substituted by the equivalent number of halogen atoms, with a chiral compound, and where the carboxylic acid function of compound II may be activated before reaction with the chiral compound, thereby forming a diastereomeric mixture of general formula IV

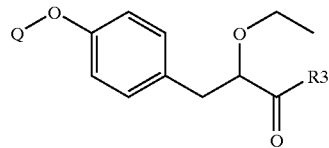

wherein Q is a protecting group or H, and R3 is a chiral auxiliary group, and one or more of the hydrogen atoms of the phenyl group are optionally substituted by the equivalent number of halogen atoms, subsequently separating the diastereomers by chromatography and/or crystallisation, thereafter, if desirable, removing the R3 group of the resulting (S)-enantiomer according to general formula IV with a suitable reagent, such as an acid or base, and, if desirable, deprotecting the Q group of the resulting (S)-enantiomer according to general formula IV with a deprotecting agent. Optionally a free carboxylic acid function may in the end be protected with the group $R^P$.

The present invention further relates to a process for the preparation of the (S)-enantiomer of a compound of the general formula VII,

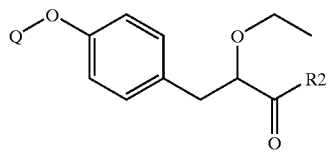

wherein Q is a protecting group or H, R2 is OH or the group $OR^P$, wherein $R^P$ is a protecting group, and one or more of the hydrogen atoms of the phenyl group are optionally substituted by the equivalent number of halogen atoms, comprising separating the enantiomers by chiral chromatography and thereafter if desirable, deprotecting the Q group of the resulting compound with a deprotecting agent, and optionally protecting a free carboxylic acid function with the group $R^P$.

The present invention further relates to a process for the preparation of a compound of the general formula VIII,

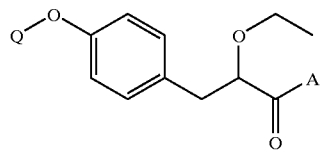

wherein Q is a protecting group or H, A is OH, a chiral auxiliary group or the group $OR^P$, wherein $R^P$ is a protecting group, and one or more of the hydrogen atoms of the phenyl group are optionally substituted by the equivalent number of halogen atoms, comprising reducing a compound according to the general formula VI

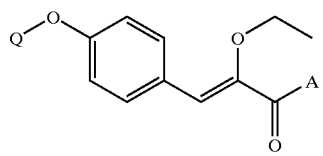

wherein Q is a protecting group or H and A is OH, a chiral auxiliary group or the group $OR^P$, wherein $R^P$ is a protecting group and one or more of the hydrogen atoms of the phenyl group may be substituted by the equivalent number of halogen atoms, by for example hydrogenation in the presence of a suitable catalyst thereby forming a compound according to the general formula VIII. Compound VIII can then be further processed as described above in connection with the preparation of a compound according to general formula I or V.

In a preferred embodiment of the present invention, A in the general formulae VI and VIII is $OR^P$ wherein $R^P$ is a protecting group selected from the group consisting of H, benzyl or $C_{1-3}$ alkyl.

In another preferred embodiment of the present invention, Q in the general formulae II–VIII is H or a protecting group selected from the group consisting of benzyl, acetyl and $C_{1-3}$ alkyl, preferably methyl.

The use of protecting groups generally is described in 'Protective Groups in Organic Synthesis', 2nd edition (1991), T. W. Greene & P. G. M. Wutz, Wiley-Interscience.

In the phenyl group of the general formulae I to VIII, one or more of the hydrogen atoms may be substituted by the equivalent number of halogen atoms, preferably chlorine or bromine or any combination thereof.

In further preferred embodiments, the deprotecting agent for Q when Q is $C_{1-3}$ alkyl is a thiol, preferably $C_{1-8}$-SH, Ph-SH or salts thereof, or an acid, preferably hydrogen bromide or hydrogen iodide.

In further preferred embodiments, the deprotecting method for Q when Q is benzyl is hydrogenation in the presence of a suitable hydrogenation catalyst, preferably a palladium catalyst, preferably palladium on carbon.

Suitable chiral amines for use in the present invention include, without limitation, (S)-(−)-1-(1-naphthyl)- ethylamine, (S)-(-)-1-(1-phenyl)-ethylamine, quine and analogues thereof, particularly quinidine, cinchonine or cinchonidine, (1R,2R)-(-)-pseudoephedrine or analogues thereof, (S)-phenyl glycinol, esters of chiral amino acids, aliphatic chiral amines or aromatic chiral amines. The most preferred chiral amine is (S)-(-)-1-(1-naphthyl)-ethylamine.

In the present invention, the compound according to general formula II is reacted with a chiral compound to give a diastereomeric mixture according to general formula IV, the diastereomers afterwards separated by chromatography and/or crystallisation, where the chiral auxiliary group is suitably a chiral amine. The chiral compound is suitably (2R)-2-amino-2-phenyl-1-ethanol or (2S)-2-amino-2-phenyl-1-ethanol.

In the present invention, the compound of the general formula III may be re-crystallized before the chiral amine is removed.

In the present invention, the compound according to general formula V is hydrolysed under acidic or basic conditions, which is suitably an inorganic acid and preferably a strong inorganic acid, such as HCl, HBr, HI, $H_2SO_4$ and/or $HNO_3$.

In the present invention, the compound according to the general formula is reduced by for example hydrogenation in the presence of a suitable catalyst, preferably palladium on carbon. The catalyst may be a chiral catalyst. Group A in the general formula VI is OH, a chiral auxiliary group or the group $OR^P$, wherein $R^P$ is a protecting group selected from the group consisting of H, benzyl or $C_{1-3}$ alkyl. The chiral auxiliary group is suitably chosen from the group of terpenes and oxazolidinones.

When deprotection of the Q group is suitable or necessary, the compound with a deprotecting group is subsequently treated with a deprotecting agent, for $C_{1-3}$ alkyl protecting groups suitably at an elevated temperature. In this context, "an elevated temperature" relates to a temperature in the range of from about 60° C. to about 180° C., suitably from 100° C. to 140° C.

The enantiomeric excess (e.e.) value is defined as $$e.e. = \frac{\text{area of } (S)\text{-isomer} - \text{area of } (R)\text{-isomer}}{\text{area of } (S)\text{-isomer} + \text{area of } (R)\text{-isomer}}$$

In the present invention, enantiomerically enriched means a compound with an e.e. value of at least about 50%, suitably at least 80%, preferably at least 90% and more preferably at least 95%.

EXAMPLES

The following Examples are intended to illustrate, but in no way limit the scope of the invention.

Example 1

Ethyl (2S)-2-ethoxy-3-(4-hydroxyphenyl)propanoate
a) Preparation of ethyl 2-ethoxyethanoate A solution of 2-chloroacetic acid (50 g, 529 mmol, 1.0 eq) in absolute ethanol (110 ml, 2.2 vol.) was charged to an ethanol solution of sodium ethoxide (494 ml, 21%, 90 g, 1.32 mol, 2.5 eq). The temperature during the charging was kept at 15–25° C. When the charging was completed the temperature was raised to 50° C. The reaction mixture was cooled to 15° C. when >95% conversion was achieved. HCl (g) was then charged until the pH of the mixture was <1. When the conversion was >95% the slurry was cooled to 15° C. and neutralized to pH 5–7 with sodium ethoxide solution (approximately 5–20% of the initially charged amount). After neutralisation the slurry was cooled to 5° C. and ethyl acetate (150 ml, 3 vol.) was charged. The sodium chloride formed in the reaction was then filtered off and washed with ethyl acetate. The solution was then evaporated. Maximum remaining ethanol was 20%.

The overall yield of the subtitle compound was 58% of the theoretical value (loss was in evaporation). The chemical purity was >99%.

b) Preparation of ethyl 2-ethoxy-3-(4-methoxyphenyl) propenoate

4-Methoxybensaldehyde (100 g, 734 mmol, 1.0 eq.) and ethyl 2-exthoxyethanoate (116 g, 881 mmol, 1.2 eq.) was dissolved in THF (600 ml, 6 vol.) under an atmosphere of nitrogen. The solution was cooled to −20° C. To the resulting solution, a solution of potassium tert-butoxide (98.8 g, 880 mmol, 1.2 eq) in THF (704 ml, 7.1 vol. corresponding to potassium tert-butoxide) was slowly charged while maintaining the temperature <−10° C. After the charging was completed, the reaction mixture was stirred for 1 hour at a temperature of −15° C. to −10° C. To the slurry, was then charged glacial acetic acid (53 g, 1.24 mol, 1.4 eq.) maintaining the temperature at <+5° C. The THF was then evaporated until about ⅓ remained. Toluene (824 ml, 8.24 vol.) was added and the rest of the THF evaporated. Water (200 ml, 2 vol.) and methanesulfonic acid (50 ml, 0.5 vol.) were added to the toluene slurry to give a pH in the water layer of 2–3. The water layer was separated off. The toluene layer was then evaporated to remove the remaining water. To the toluene solution was added methanesulfonic acid (2.11 g, 22 mmol, 0.03 eq). The toluene solution was refluxed with a Dean-Starke device connected until full conversion was achieved. The solution was cooled to 25° C. The solution was then washed with sodium hydroxide (aq, 48%) (1.83 g, 22 mmol, 0.03 eq.) diluted in water (15 ml).

The overall yield of the subtitle compound was approximately 52% of the theoretical value.

c) Preparation of 2-ethoxy-3-(4-methoxyphenyl)propenoic acid

NaOH (aq., 48%) (122 g, 1.46 mol, 2.0 eq.), water (244 ml, 2.44 vol.) and EtOH (90 ml, 0.9 vol.) were charged to the toluene solution of ethyl 2-ethoxy-3-(4-methoxyphenyl) propenoate (approximately 96 g, 382 mmol, 0.52 eq.). The reaction mixture was heated to 50° C. and stirred until full conversion was achieved. After the reaction was complete, the toluene layer was separated off and the water layer was then washed with toluene (100 ml, 1 vol.). After separation, the water layer was cooled to +5° C. and acidified with conc. HCl (approximately 173 ml, 2.1 mol, 2.9 eq.). The temperature was kept <10° C. during the charging of the acid. EtOAc (100 ml, 1 vol.) was added to the acidic water slurry. After extraction the phases were separated. The EtOAc solution was evaporated and toluene (288 ml, 3 vol.) was added. The toluene solution was seeded with 2-ethoxy-3-(4-methoxyphenyl) propenoic acid, and cooled to 0° C. After crystallisation the material was filtered. The wet substance was used without drying in the subsequent step.

The overall yield of the subtitle compound was 42% of the theoretical value for step b & c together. The chemical purity was 99.7%.

d) Preparation of 2-ethoxy-3-(4-methoxyphenyl)propanoic acid

Palladium on charcoal (5%, 60% water wet) (13.2 g, 0.26 g Pd, 2.44 mmol Pd, 0.0054 eq.) was charged to a solution of 2-ethoxy-3-(4-methoxyphenyl)propenoic acid (100 g, 450 mmol, 1.0 eq.) in ethanol (800 ml, 8 vol.) under a nitrogen atmosphere. The vessel was then pressurized with hydrogen to 4 bar total pressure. The hydrogenation was continued until full conversion was achieved. The catalyst was filtered off and the ethanol was evaporated under vacuum. Toluene (500 ml, 5 vol.) was added and then evaporated off. The residue was dissolved in toluene (500 ml, 5 vol.) and evaporated to a volume of 260 ml. The solution was heated to 50° C. and isooctane (800 ml, 8 vol.) was added. The solution was cooled to 35° C. and then seeded with 2-ethoxy-3-(4-methoxyphenyl)propanoic acid. The temperature was maintained at 35° C. for 30 min. The thin slurry was then cooled at a rate of 10° C./hour down to +5° C. which was maintained overnight. The crystals were then filtered off and washed with isooctane (220 ml, 2.2 vol.) The crystals were dried under vacuum at 30° C.

The yield of the subtitle compound was 88% of the theoretical value. The chemical purity was 99.8%.

e) Preparation of (1S)-1-(1-naphthyl)-1-ethanaminium (2S)-2-ethoxy-3-(4-methoxyphenyl) Propanoate A solution of 2-ethoxy-3-(4-methoxyphenyl)propionic acid (100 g, 446 mmol, 1.0 eq.) in i-PrOAc (2000 ml, 20 vol.) was stirred at 0–5° C. under a nitrogen atmosphere. (S)-(−)-1-(1-naphthy) ethylamine (45.8 g, 268 mmol, 0.6 eq.) was added to the resulting solution. The resulting suspension was heated to 75–80° C. to dissolve all particles, thereby achieving a solution. The solution was then cooled and seeded with (2S)-2-ethoxy-3-(4-methoxyphenyl) propanoic acid (S)-(−)-1-(1-naphthyl) ethylamine salt. The desired diastereomeric salt was collected by filtration. The crystals were washed with i-PrOAc.

The (2S)-2-ethoxy-3-(4-methoxyphenyl)propanoic acid (S)-(−)-1-(1-naphthyl) ethylamine salt obtained (67 g, 169 mmol, 1.0 eq.) was dissolved by heating to 75–80° C. in isopropylacetate (1340 ml, 20 vol.). The product obtained was collected by filtration, washed with isopropylacetate and dried under vacuum, at 40° C., to a constant weight.

The overall yield over the two crystallisation steps was 74% of the theoretical value. The chemical purity was >99%. The enantiomeric excess (e.e.) was 97.8%.

f) Preparation of (2S)-ethoxy-3-(4-hydroxyphenyl) propanoic acid (2S)-2-ethoxy-3-(4-methoxyphenyl)propanoic acid (S)-(−)-1-(1-naphthyl)ethylamine salt (100 g, 253 mmol, 1.0 eq.) was suspended in toluene. The mixture was then treated with NaOH (11.1 g, 278 mmol, 1.1 eq.) in water (280 ml, 5 vol.). The upper toluene layer containing the chiral amine was separated. The lower aq. layer was washed with two more portions of toluene (280 ml, 5 vol.). The lower aq. layer was acidified to pH=1 with aq. 37% HCl (30 g, 304 mmol, 1.2 eq.). The water solution containing (S)-2-ethoxy-3-(4-methoxyphenyl)propanoic acid was extracted with two portions of EtOAc (280 ml, 5 vol.). The combined EtOAc extract was washed with one portion of water (280 ml, 5 vol.). The solvent was replaced with NMP under reduced pressure.

NaOH (beads) (45.5 g, 1.14 mol, 4.5 eq.) and octanethiol (129 g, 154 ml, 884 mmol, 3.5 eq.) were charged to the solution of (S)-2-ethoxy-3-(4-methoxyphenyl)propanoic acid (approximately 56.6 g, 253 mmol, 1.0 eq.) in NMP (680 ml, 12 vol.) under a nitrogen atmosphere. The reaction mixture was heated to 120° C. and kept at 115–125° C. until the reaction was complete as determined by HPLC.

The reaction mixture was cooled to 60° C. and then quenched with water. The pH was then adjusted to 2–3 with conc. HCl. The temperature was maintained at 60–70° C. Two layers were formed, the upper layer of which containing mainly octanethiol and the corresponding methyl ether (formed in the reaction). The layers were separated and the layer containing water and NMP was concentrated to 3–4 volumes under vacuum at 80–100° C. inner temperature.

The residue was extracted with a mixture of $H_2O$:EtOAc. The EtOAc solution was subsequently washed 3 times with a 15% NaCl solution. The EtOAc was evaporated and the residue was directly used in the subsequent step or could also be crystallized from toluene to yield a white solid.

The yield was 52% using crystallisation, 90% using only evaporation. The chemical purity was 99.8%. The enantiomeric excess (e.e.) was 97.8%.

g) Preparation of ethyl (2S)-2-ethoxy-3-(4-hydroxyphenyl) propanoate (2S)-2-ethoxy-3-(4-hydroxyphenyl)propanic acid (874 g, 4.16 mol, 1.0 eq.) was dissolved in EtOAc (1250 ml). To this solution were charged ethanol (3000 ml) and HCl (37%, aq.) (40 ml, 0.48 mol. 0.12 eq.). The solution was heated to boiling (about 72° C.) and water/EtOAc/EtOH (2000 ml) was distilled off. Another portion of EtOH (2000 ml) was charged and another 2000 ml was distilled off. This procedure was repeated once more. At this point approximately 95% conversion was reached. Then EtOH (99.5%, 1000 ml) was added and evaporated off. This was repeated until a conversion of >97.5% was achieved. The solution was then concentrated to a volume of 1700–2000 ml under vacuum and then cooled to 20° C.

The EtOAc solution containing ethyl (S)-2-ethoxy-3-(4-hydroxyphenyl)propanoate was then charged slowly (30–40 min) under vigorous stirring to a solution of $NaHCO_3$ (7% w/w, 3500 ml). Crystallisation occured after a few minutes. After charging, the slurry was cooled to 0–5° C. and then stirred at 0–5° C. for at least one hour. The crystals were then filtered off and dried under vacuum.

The yield was about 93%. The chemical purity was >99%. The enantiomeric excess (e.e.) was >97.8%.

Example 2

Ethyl (2S)-2-ethoxy-3-(4-hydroxyphenyl)propanoate a) Preparation of Ethyl 2-chloro-2-ethoxy ethanoate Ethyl 2,2-diethoxy ethanoate (47.5 kg, 263 mol) was treated for 20 h at 60° C. with iodine (0.1 kg) and acetylchloride (21.9 kg, 279 mol, addition time 2 h). The resulting low boiling reaction by-products were distilled off at 40° C./170 mbar resulting in a dark-colored liquid (50 kg, GLC: 89% area, 100% yield (content corrected).

b) Preparation of (1,2-Diethoxy-2-oxoethyl)(triphenyl) phosphonium chloride

Ethyl 2-chloro-2-ethoxy ethanoate (50 kg, 268 mol) was added over 70 min at 20–30° C. to a solution of triphenylphosphine (71.6 kg, 261.8 mol) dissolved in $CH_2Cl_2$ (102 L). For 13 h the reaction was kept at 20° C. $CH_2Cl_2$ was then distilled off and TBME (230 L) was added. Upon seeding the material crystallized in big clusters that could not be removed from the reactor. The liquid parts were decanted off. The material was then dried in the reactor by distilling off remaining TBME (jacket temperature of 40° C. and full vacuum). From an aliquot of the original suspension the yield was calculated to be 100% (128 kg, GLC: 92% area).

c) Preparation of Ethyl 3-[4-(benzyloxy)phenyl]-2-ethoxy-2-propenoate

The crystals of (1,2-diethoxy-2-oxoethyl)(triphenyl) phosphonium chloride in the reactor were dissolved in $CH_2Cl_2$ (290 L) followed by the addition of 4-benzyloxybenzaldehyde (44.2 kg, 208 mol, yield is based on this chemical). To this solution tetramethylguanidine (25.4 kg, 220 mol) was added in 1 hour. The solution was then stirred for 20 hours at 20° C. $CH_2Cl_2$ (200 L) was distilled off and at an T$_i$ of 30° C. replaced TBME (280 l). The crystals of TPPO formed were filtered off at 20° C. and the mother-liquor was concentrated until a new precipitate was formed. The TPPO was filtered off again and the mother-liquor was concentrated until no more solvents distilled. 2-Propanol (260 L) and seeding crystals (ethyl 3-[4-(benzyloxy)phenyl]-2-ethoxy-2-propenoate) (50 g) were added before cooling to 0° C. The resulting suspension was filtered and the isolated material dried at 40° C./160 mbar. The overall yield was 44.5 kg, 65% (GLC: 99% area).

d) Preparation of Ethyl 3-[4-(benzyloxy)phenyl]-2-ethoxy-2-propanoate

Ethyl 3-[4-(benzyloxy)phenyl]-2-ethoxy-2-propenoate was converted to ethyl 3-[4-(benzyloxy)phenyl]-2-ethoxy-2-propanoate in two identically sized trials. Ethyl 3-[4-(benzyloxy)phenyl]-2-ethoxy-2-propenoate (16 kg 48.5 mol) was dissolved in EtOAc (80 L) and Pd/C 10% (0.79 kg) suspended in EtOAc (2.5 L) was added. The vessel was inertised and filled with H$_2$. The hydrogenation was initiated by starting the stirrer and lasted 26 hours. The catalyst was filtered off (glass filter/Cellite (2.5 kg)). The filtrates of both trials were combined and washed with 1 M NaOH (60 L) and saturated NaCl solution (20 L). The clear organic phase was concentrated in vacuo/50° C. to yield 30.6 kg, 91% ethyl 3-[4-(benzyloxy) phenyl]-2-ethoxy-2-propanoate (GLC 94.4% area).

e) Preparation of 3-[4-(benzyloxy)phenyl]-2-ethoxypropanoic Acid

Ethyl 3-[4-(benzyloxy)phenyl]-2-ethoxy-2-propanoate (30.6 kg, 87.9 mol) was dissolved in EtOH (205 L). NaOH 30% (15.6 kg, 114 mol) was added in 12 min, The clear solution was stirred for 9 h at 20° C. and 3 hours at 0° C. Water (91 L) was added and EtOH distilled off (195 L, jacket temperature 40° C./110 mbar). TBME (122 L) was added and the emul-sion cooled to 0° C. To the well stirred emulsion, H$_2$SO$_4$ (46 L) was added in 50 minutes. The layers were separated and the aqueous layer extracted with TBME (122 L). The combined organic layers were washed with saturated NaCl solution (62 L) and concen-trated in vacuo/45° C. to yield 30.6 kg, 100% (GLC 89% area).

f) Preparation of 3-[4-(benzyloxy)Phenyl]-2-ethoxy-N-[(1R)-2-hydroxy-1-phenylethyl]propanamide 3-[4-(Benzyloxy)phenyl]-2-ethoxypropanoic acid (30.6 kg, 88 mol) and DMAP (12.9 kg) were dissolved in CH$_2$Cl$_2$ (192 L) and cooled to 0° C. To the clear solution EDCxHCl (20.2 kg) was added in 10 minutes. In 18 minutes a solution of (2R)-2-amino-2-phenyl-1-ethanol (14.5 kg, 105.6 mol) in CH$_2$Cl$_2$ (60 L) was added, keeping the temperature below 2° C. The reaction mixture was kept at 0° C. for 2 hours and then heated to reflux for ca. 3 hours. The solvent was then distilled off (110 L). EtOAc (110 L) was added and the temperature lowered to 10° C. Over 30 min 1M H$_2$SO$_4$ (110 L, 110 mol) was added, the phases separated and the organic phase extracted with H$_2$SO$_4$ (110 L, 110 mol). To the combined organic phases, 110 L EtOAc and 1 M NaOH (110 L, 110 mol) were added at 10° C. (pH 10). The phases were separated and the organic phase washed with saturated NaCl solution.

g) Preparation of (2S)-3-[4-(benzyloxy)phenyl]-2-ethoxy-N-[(1R)-2-hydroxy-1-phenylethyl]propanamide The EtOAc was distilled off (460 L) to yield a white suspension that was filtered, washed six times with EtOAc/heptane 1:1 (totally 15 L). The filtercake was set aside ((R) isomer) and the mother-liquor concentrated to yield 22.15 kg, 54% (GLC 51.7% (2S)-3-[4-(benzyloxy) phenyl]-2-ethoxy-N-[(1R)-(2-hydroxy-1-phenylethyl]propanamide, 21.8% (2R)-3-[4-(benzyloxy)phenyl]-2-ethoxy-N-[(1R)-2-hydroxy-1-phenylethyl]propanamide).

The crude enriched material (14.4 kg) was chromatographed in two batches over silica gel (totally 80 kg) using MeOH/CH$_2$Cl$_1$ :99 (800 L) as mobile phase. A total of 4.4 kg, 51% (93% chemical purity, pure (2S)-3-[4-(benzyloxy) phenyl]-2-ethoxy-N-[(1R)-(2-hydroxy-1-phenylethy] propanamide enantiomer) was obtained.

h) Preparation of (2S)-3-[4-(benzyloxy)phenyl]-2-ethoxypropanoic acid (2S)-3-[4-(benzyloxy)phenyl]-2-ethoxy-N-[(1R)-2-hydroxy-1-phenylethyl ]propanamide (4.3 kg, 10.2 mol) were dissolved in dioxane (30 L) and diluted with deionized water (35 L). To this opaque reaction mixture, H$_2$SO$_4$ (19.2 kg, 192 mol) was added. The reaction temperature was raised to 80° C. and kept at 80° C. for 15 hours. The reaction mixture was extracted twice with TBME (64 L, 70 L) at room temperature. The combined organic phases were extracted twice with 1 M NaOH (2×20 L, 2×20 mol). The aqueous phases were acidified with H$_2$SO$_4$ (24 L, 24 mol), extracted with TBME (40 L) and the organic phases dried with saturated NaCl solution. The solution was concentrated to yield 64 L concentrate which contained 2.9 kg, 100% (GLC 68% area (2S)-3-[4-(benzyloxy) phenyl]-2-ethoxypropanoic acid and 28% area (2S)-2-ethoxy-(4-hydroxyphenyl) propanoic acid).

i) Preparation of (2S)-2-ethoxy-(4-hydroxyphenyl) propanoic acid

To the TBME solution of (2S)-3-[4-(benzyloxy)phenyl]-2-ethoxypropanoic acid, 10% Pd/C (totally 204 g) was added and 0.2 bar hydrogen pressure applied. The hydrogenation lasted 2 hours. The catalyst was filtered off and the solution concentrated (50° C./12 mbar final pressure). Since this crude oil still contained 12% area toluene (by GLC) the residual oil was stripped 5 times with EtOH (5×1 L) until no more toluene was detected in the crude material. 2.2 kg, 92% (GLC: 96% area) of slowly crystallizing oil was obtained.

j) Preparation of ethyl (2S)-2-ethoxy-(4-hydroxyphenyl) propanoate

Gaseous HCl (2.95 kg) was absorbed into EtOH (10 L) at 0°-4° C. (titrated final content: 24.7% w/v). The temperature rose towards the end to 17° C. at which (2S)-2-ethoxy-(4-hydroxyphenyl) propanoic acid (2.08 kg, 9.9 mol) was added. The temperature was increased to 80° C. and thionyl chloride (1.97 kg, 14.8 mol) was added carefully over 1 hour. The clear solution was kept at reflux for 2 hours and then stirred at 20° C. for 10 h. The solution was then concentrated in vacuo/40° C. to yield 1.98 kg crude ethyl (2S)-2-ethoxy-3-(4-hydroxy propanoate (slowly crystallizing oil). The crude material was dissolved in EtOAc (10 L) and heptane (31 L) and filtered through silica gel (4.0 kg). The silica was washed with EtOAc/heptane=1:3 (12 L) and the filtrate concentrated (45° C./30 mbar) to yield 1.8 kg crystallizing oil. To this EtOAc (1.2 L) and heptane (3.6 L) was added, heated to 40° C. to obtain a clear solution and slowly cooled to 20° C. Occasionally while cooling down seeding crystals (ethyl (2S)-2-ethoxy-3-(4-hydroxyphenyl) propanoate) (pure enantiomer) were added. After 2 hours at 0–2° C. the crystals were filtered off, washed with EtOAc/heptane=1:3 (2.0 L) in 3 portions (0° C.), EtOAc/heptane= 1:7 (2.0 L) in 4 portions (0° C.) and heptane (1.6 L). The off-white crystals were dried on a rotary evaporator (40° C./15 mbar, constant weight) to yield 1.09 kg, 48% (GLC: 98.4% area., ee-HPLC 98.7% area).

Example 3

Ethyl (2S)-2-ethoxy-(4-hydroxyphenyl)propanoate
f) Preparation of 3-[4-(benzyloxy)phenyl]-2-ethoxy-N-[(1S)-(2-hydroxy -1-phenylethyl ]propanamide 3-[4-(benzyloxy)phenyl]-2-ethoxy-N-[(1S)-(2-hydroxy-1-phenylethyl]propanamide was prepared according to step a) to f) in Example 2, using (2S)-2-amino-2-phenyl-1-ethanol.

g) Preparation of (2S)-3-[4-(benzyloxy)phenyl]-2-ethoxypropanoic acid

The diastereomeric mixture (21.6 kg, 51.6 mol, (2S)-3-[4-(benzyloxy)phenyl]-2-ethoxy-N-[(1S)-(2-hydroxy-1-phenylethyl]propanamide/(2R)-3-[4-(benzyloxy)phenyl]-2-ethoxy-N-[(1S)-(2-hydroxy-1-phenylethyl]propanamide) was suspended in ethyl acetate (113 L) and heated to reflux for 30 min. The solution was slowly (1 h) cooled to 36–40° C. and heptane (113 L) was added under vigorous stirring over 2 h. The mixture was cooled to 15° C. over 4 h.

The material was filtered off and washed with a mixture of ethyl acetate and heptane (1:1; 113 L) to yield 5.36 kg of a white solid (HPLC: 97.2% area (2S)-3-[4-(benzyloxy)phenyl]-2-ethoxy-N-[(1S)-(2-hydroxy-1-phenylethyl]propanamide; 2.8% area (2R)-3-[4-(benzyloxy)phenyl]-2-ethoxy-N-[(1S)-(2-hydroxy-1-phenylethyl]propanamide).

h) Preparation of (2S)-3-[4-(benzyloxy)phenyl ]-2-ethoxypropanoic acid

To the reactor was charged deionized water (35.7 L), via the dropping funnel conc. $H_2SO_4$ (10 L; 178.97 mol) was added under cooling (the inner temperature was maintained below 10° C.). The solution was transferred to a dropping funnel and the reactor was charged with 1,2-Dimethoxyethane (49.5 L) and (2S)-3-[4-(benzyloxy)phenyl]-2-ethoxy-N-[(1S)-(2-hyroxy-1-phenylethyl]propanamide (5.363 kg; 12.78 mol; enantiomeric purity: HPLC: 96.5% (2S)-3-[4-(benzyloxy)phenyl]-2-ethoxy-N-[(1S)-(2-hydroxy-1-phenylethyl]-propanamide; 3.5% (2R)-3-[4-(benzyloxy)phenyl]-2-ethoxy-N-[(1S)-(2-hydroxy-1-phenylethyl]propanamide).

To the white suspension the $H_2SO_4$ solution was added over 1 h (inner temperature 20° C.). The reaction mixture was heated to 80° C. (jacket temperature: 90° C.) for 15 h. The reaction mixture was cooled to 20° C., TBME (85 L) was added, the mixture was stirred for 20 min and the phases were separated. The aqueous layer was extracted with TBME (84 L). The organic layers were combined and extracted three times with 1 M NaOH (23 L, 23 L. 15 L). The aqueous layers were combined and 1 M $H_2SO_4$ was added until pH 1 was achieved (46.5 L were necessary).

The aqueous phase was extracted with TBME (80 L). After drying with $Na_2SO_4$ (3.37 kg), the solvent was removed under reduced pressure to obtain 4.087 kg of (2S)-3-[4-(benzyloxy) phenyl]-2-ethoxypropanoic acid (enantiomeric purity: HPLC: 96.6% area (2S)-3-[4-(benzyloxy)phenyl]-2-ethoxypropanoic acid).

i) Preparation of ethyl (2S)-2-ethoxy-(4-hydroxyphenyl)propanoate

The reactor was charged with ethanol (12 L), HCl gas was bubbled through for 7 h. The inner temperature was kept below 10° C.—intensive cooling was necessary. By titration, the content of HCl was determined to be 32.9%. 5 L of the ethanolic HCl were removed, to the residual amount (ca. 10 L) (2S)-3-[4-(benzyloxy)phenyl]-2-ethoxypropanoic acid (4.08 kg, 12.78 mol, calculated on the assumption of 100% yield in the former step h) was added. The suspension was slowly (over 1 h) warmed up to 20° C. To the resulting solution, thionylchloride (1.85 L, 25.56 mol, 2 equiv.) was added over 30 min—gas was developed heavily. The reaction mixture was slowly heated (jacket temperature: 65° C.). At 35° C. inner temperature the development of gas was so vigorous, that the washer was overburdened. The heating was stopped and the inner temperature was kept at 35° C. for 15 min. Then heating was continued and the reaction mixture was kept under reflux for 2 h 30 min. Since conversion was not complete (GC: 46.6% of (2S)-ethoxy-3-(4-hydroxyphenyl)propanoic acid), additional ethanolic HCl (5 L) and additional thionylchloride (1 L, 13.81 mol) was added and heating was continued for 12 h. Still conversion was not complete (GC: 5.3% of (2S)-ethoxy-3-(4-hydroxyphenyl)propanoic acid) and HCl-gas was bubbled through the reaction solution at 0–5° C. for 2 h. Then heating to reflux was continued for 2 h 30 min. Nearly complete conversion was achieved (GC: 1.1% of (2S)-ethoxy-3-(4-hydroxyphenyl)propanoic acid). The solvent was removed by distillation under reduced pressure (jacket temperature: 40–50° C.; 250–40 mbar).

The remaining oil (3.778 kg, GC: 70.6% of ethyl (2S)-2-ethoxy-(4-hydroxyphenyl)-propanoate; chiral purity: 96.7% of ethyl (2S)-2-ethoxy-(4 -hydroxyphenyl) propanoate) was dissolved in ethyl acetate (11 L). The solution was washed with $NaHCO_3$ (10.5 L). The aqueous phase was re-extracted twice with ethyl acetate (2×7 L). The organic layers were combined, dried with $Na_2SO_4$ (1.276 kg) and the solvent was removed in vacuum jacket temperature: 40° C.; 150–50 mbar) to yield 3.76 kg of a brown oil.

The crude product was dissolved in ethyl acetate (3.5 L), under vigorous stirring heptane (7 L) was added over 20 min at 20–23° C. (inner temperature). The solution was slowly (over 1 h 35 min) cooled to 0° C. No precipitation was observed and the solution was seeded with 1.6 g of ethyl (2S)-2-ethoxy-(4-hydroxyphenyl)propanoate and cooled to −5° C. over 2 h. The suspension was stirred for 22 h at −5° C. The solid was filtered off and washed with heptane (6 L). After drying (24 h, jacket temperature: 40° C.) 1.578 kg of a beige solid was obtained (GC: 99.5% area; HPLC: chiral purity: 100% ). Yield: 52% (calculated on (2S)-3-[4-(benzyloxy) phenyl]-2-ethoxy-N-[(1S)-(2-hydroxy-1-phenylethyl]propanamide.

The mother liquor was reduced (6 L of solvent were distilled off). At 15° C. ethyl acetate (0.5 L) was added and the cloudy solution was cooled to 2° C. and stirring was continued for 15 h. The suspension was filtered off and washed with heptane (4 L). The brown solid (wet, 295.2g) was re-crystallized from ethyl acetate (300 mL) and heptane (900 mL) to yield after drying 155.8 g of a beige solid (GC purity: 97.7% area.; chiral HPLC e.e.: 100%).

1055.6 g of ethyl (2S)-2-ethoxy-(4-hydroxyphenyl) propanoate were suspended in ethyl acetate (685 mL) and in heptane (2055 mL). At 38° C. inner temperature a clear solution was achieved. The solution was cooled slowly (1 h 20 min) to 27° C. inner temperature The solution was seeded with 1 g of ethyl (2S)-2-ethoxy-(4-hydroxyphenyl) propanoate. Cooling was continued to 0° C. within 1 h 30 min. Precipitation started at 15° C. The suspension was filtered off and washed with heptane/ethyl acetate 7:1 (1L). After drying, 783.4g (GC: 98.7%) of a beige powder were obtained.

Abbrevations

DMAP=N,N-dimethylaminopyridine
DMF=dimethyl formamide
EDC=1-(3-Dimethylaminopropyl)-3-ethylcarbodiimide hydrochloride
e.e.=enantiomeric excess
Et=ethyl
EtOAc=ethyl acetate
GLC=gas-liquid chromatography
HPLC=high-pressure liquid chromatography
i-PrOAc=isopropyl acetate NMP=N-methyl-2-pyrrolidinone
Ph=phenyl
TBME=tert-butyl methyl ether
THF=tetrahydrofuran
TPPO=Triphenyl phosphine oxide

What is claimed is:

1. A process for the preparation of the (S)-enantiomer of a compound of formula I,

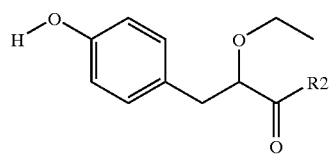

I wherein R2 is OH or the group $OR^P$, wherein $R^P$ is a protecting group, and one or more of the hydrogen atoms of the phenyl group may optionally be substituted by the equivalent number of halogen atoms, comprising reacting a racemic compound according to formula II

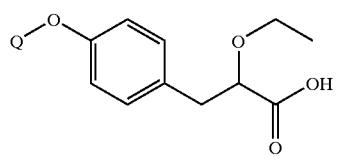

II wherein Q is a protecting group or H, and one or more of the hydrogen atoms of the phenyl group are optionally substituted by the equivalent number of halogen atoms, with a chiral amine, thereby forming a salt according to formula III

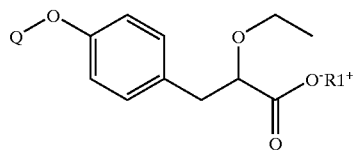

III wherein Q is a protecting group or H, and R1 is a chiral amine, and one or more of the hydrogen atoms of the phenyl group are optionally substituted by the equivalent number of halogen atoms, subsequently separating the diastereomers by crystallization followed by removal of the amine, and thereafter, when Q represents a protecting group, removing the Q group of the resulting compound with a deprotecting agent, and optionally protecting a free carboxylic acid function with the group $R^P$.

2. The process according to claim 1, wherein the chiral amine is (S)-(−)-1-(1-naphthyl)-ethylamine.

3. The process according to claim 1, wherein the compound of formula III is recrystallised before the chiral amine is removed.

4. A process for the preparation of the (S)-enantiomer of a compound of formula V,

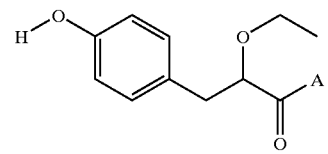

V wherein A is OH, a chiral auxiliary group or the group $OR^P$, wherein $R^P$ is a protecting group, and one or more of the hydrogen atoms of the phenyl group are optionally substituted by the equivalent number of halogen atoms, comprising reacting a racemic compound according to formula II

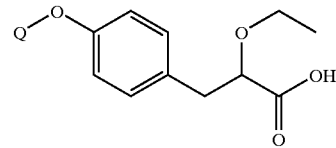

II wherein Q is a protecting group or H, and one or more of the hydrogen atoms of the phenyl group are optionally substituted by the equivalent number of halogen atoms, with a chiral compound, thereby forming a diastereomeric mixture of formula IV

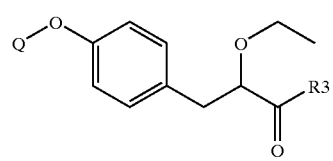

IV wherein Q is a protecting group or H, and R3 is a chiral auxiliary group, and one or more of the hydrogen atoms of the phenyl group are optionally substituted by the equivalent number of halogen atoms, subsequently separating the diastereomers by chromatography and/or crystallization, thereafter, removing the R3 group of the resulting (S)-enantiomer according to formula IV with a suitable reagent selected from an acid or base, and, when Q represents a protecting group, removing the Q group of the resulting (S)-enantiomer according to formula IV with a deprotecting agent, and optionally protecting a free carboxylic acid function with the group $R^P$.

5. The process according to claim 4, wherein the chiral compound is a chiral amine or a chiral alcohol.

6. A process for the preparation of the (S)-enantiomer of a compound of formula VII,

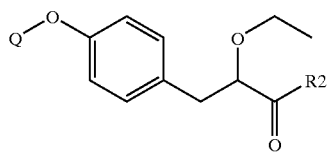

VII wherein Q is a protecting group or H, R2 is OH or the group $OR^P$, wherein $R^P$ is a protecting group, and one or more of the hydrogen atoms of the phenyl group are optionally substituted by the equivalent number of halogen atoms, comprising separating the enantiomers by chiral chromatography and optionally protecting a free carboxylic acid function with the group $R^P$.

7. The process according to any one of claims 1–6, wherein $R^P$ is a protecting group selected from the group consisting of H, benzyl and $C_{1-3}$ alkyl.

8. The process according to any one of claims 1–6, wherein Q is a protecting group selected from the group consisting of benzyl, acetyl and $C_{1-3}$ alkyl.

9. The process according to claim 8, wherein Q is $C_{1-3}$ alkyl and the deprotecting agent is a thiol.

10. The process according to claim 9, wherein the thiol is selected from the group consisting of $C_{1-8}$—SH, Ph-SH and salts thereof.

11. The process according claim 8, wherein Q is $C_{1-3}$ alkyl and the deprotecting agent is an acid.

12. The process according, to claim 11, wherein the acid is hydrogen bromide or hydrogen iodide.

13. The process according to claim 9, wherein the temperature in the deprotecting step lies in the range of from about 60° C. to about 180° C.

14. The process according to claim 8, wherein Q is benzyl and the deprotecting method is hydrogenation in the presence of a catalyst.

15. The process according to any one of claims 1, 4 or 6, wherein the one or more halogen atoms of formulae I–VIII are selected from the group consisting of chlorine and bromine and any combination thereof.

16. A compound of formula VI

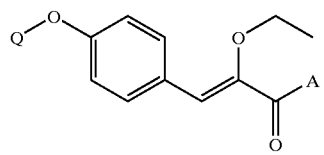

wherein Q is a protecting group or H, and A is OH, a chiral auxiliary group or the group $OR^P$, wherein $R^P$ is a protecting group, and one or more of the hydrogen atoms of the phenlyl group is substituted by the equivalent number of halogen atoms.

17. The compound according to claim 16, wherein $R^P$ is a protecting group selected frown the group consisting of H, benzyl and $C_{1-3}$ alkyl.

18. The compound according to claim 16 or 17, wherein the one or more halogen atoms are selected from the group consisting of chlorine and bromine and any combination thereof.

19. The process according to claim 2, wherein the compound of formula III is recrystallised before the chiral amine is removed.

20. The process according to claim 4, wherein the chiral compound is (2R)-2-amino-2-phenyl-1-ethanol.

21. The process according to claim 4, wherein the chiral compound is (2S)-2-amino-2-phenyl-1-ethanol.

22. The process according to claim 19, wherein $R^P$ is a protecting group selected from the group consisting of H, benzyl and $C_{1-3}$ alkyl.

23. The process according to claim 20, wherein $R^P$ is a protection group selected from the group consisting of H, benzyl and $C_{1-3}$ alkyl.

24. The process according to claim 21, wherein $R^P$ is a protecting group selected from the group consisting of H, benzyl and $C_{1-3}$ alkyl.

25. The process according to claim 19, wherein Q is a protecting group selected from the group consisting of benzyl, acetyl and $C_{1-3}$ alkyl.

26. The process according to claim 20, wherein Q is a protecting the group selected from the group consisting of benzyl acetyl and $C_{1-3}$ alkyl.

27. The process according to claim 21, wherein Q is a protecting group selected from the group consisting of benzyl, acetyl and $C_{1-3}$ alkyl.

28. The process according to claim 22, wherein Q is a protecting group selected from the group consisting of benzyl, acetyl and $C_{1-3}$ alkyl.

29. The process according to claim 23, wherein Q is a protecting group selected from the group consisting of benzyl, acetyl and $C_{1-3}$ alkyl.

30. The process according to 24, wherein Q is a protecting group selected from the group consisting of benzyl, acetyl and $C_{1-3}$ alkyl.

31. A process for the preparation of the (S)-enantiomer of a compound of formula I,

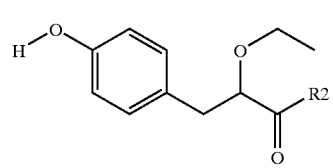

wherein R2 is OH or the group $OR^P$, wherein $R^P$ is a protecting group, comprising reacting a racemic compound according to formula II

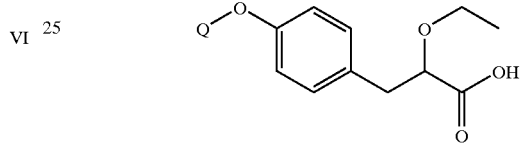

wherein Q is methyl with (S)-(–)-1-(1-naphthyl)-ethylamine thereby forming a salt according to formula III

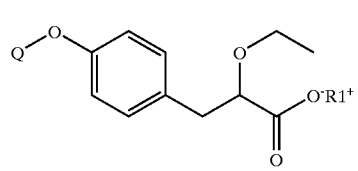

wherein Q is methyl, and R1 is (S)-(–)-1-(1-naphthyl)-ethylamine, subsequently separating the diastereomers by crystalliation followed by removal of the amine, and thereafter removing the Q group of the resulting compound with a deprotecting agent, and optionally protecting a free carboxylic acid function with the group $R^P$.

32. The process according to claim 31, wherein the compound of formula III is recrystallised before the chiral amine is removed.

33. The process according to claim 31, wherein $R^P$ is a protecting group selected from the group consisting of H, benzyl and $C_{1-3}$ alkyl.

34. The process according to any one of claims 31, 32, or 33, wherein the deprotecting agent is a thiol.

35. The process according to claim 34, wherein the thiol is selected from the group consisting of $C_{1-8}$—SH, Ph-SH and salts thereof.

36. The process according to any one of claims 31, 32, or 33, wherein the deprotecting agent is an acid.

37. The process according to claim 36, wherein the acid is hydrogen bromide or hydrogen iodide.

38. The process according to claim 35, wherein the temperature in the deprotecting step lies in the range of from about 60° C. to about 180° C.

39. The compound (1S)-1-(1-naphthyl)-1-ethanaminium (2S)-2-ethoxy-3-(4-methoxyphenyl)propanoate.

* * * * *